(12) United States Patent
Latli et al.

(10) Patent No.: US 6,303,638 B1
(45) Date of Patent: Oct. 16, 2001

(54) SUBSTITUTED PYRIDINES AS MODULATORS OF THE MAMMALIAN NEURONAL NICOTINIC ACETYLCHOLINE RECEPTOR

(75) Inventors: Bachir Latli, Danbury, CT (US); John E. Casida, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/372,114

(22) Filed: Aug. 20, 1999

Related U.S. Application Data

(60) Provisional application No. 60/147,630, filed on Aug. 6, 1999.

(51) Int. Cl.$^7$ .................... C07D 417/06; A61K 31/4427
(52) U.S. Cl. .................... 514/340; 514/275; 514/218; 514/226.8; 514/227.2; 514/318; 514/341; 514/342; 514/343; 546/193; 546/270.7; 546/271.4; 546/274.7; 546/279.1; 544/33; 544/55; 540/553
(58) Field of Search ............... 546/270.7, 271.4, 546/274.7, 219.1; 514/340, 341, 342, 343, 275, 218, 226.8, 227.2, 318; 544/333, 55; 540/553

(56) References Cited

U.S. PATENT DOCUMENTS 5,852,041    12/1998    Cosford et al. .................. 514/351

FOREIGN PATENT DOCUMENTS

WO 99/24422    5/1999    (WO) .

OTHER PUBLICATIONS

Bannon et al., "Broad–Spectrum, Non–Opioid Analgesic Activity by Selective Modulation of Neuronal Nicotinic Acetylcholine Receptors," *Science* 279:77–81 (Jan. 2, 1998).

Chao et al. (1997), "Interaction of Imidacloprid Metabolites and Analogues with the Nicotinic Acetylcholine Receptor of Mouse Brain in Relation to Toxicity," *Pestic. Biochem. Physiol.* 58:77–88.

Latli et al. (1999), "Novel and Potent 6–Chloro–3–pyridinyl Ligands for the α4β2 Neuronal Nicotinic Acetylcholine Receptor," *J. Med. Chem.* 42:2227–2234.

Latli et al. (1998), "Novel and Potent 6–Chloro–3–pyridinylmethyl Ligands for the α4β2 Neuronal Nicotinic Acetylcholine Receptor," jointly published as AGRO 74 and MEDI 151 at the American Chemical Society National Meeting, Aug. 23, 1998.

Tomisawa et al. (1999), "Minor Structrual Changes in Nicotinoid Insecticides Confer Differential Subtype Selectivity for Mammalian Nicotinic Acetylcholine Receptors," *Br. J. Pharmacol.* 127:115–122.

*Primary Examiner*—Jane Fan
(74) *Attorney, Agent, or Firm*—Dianne E. Reed; Reed & Associates

(57) ABSTRACT

Novel compounds are provided that modulate the neuronal nicotinic acetylcholine receptor (nAChR), particularly the mammalian nAChR (m-nAChR). The compounds are substituted pyridine derivatives such as analogs of 1-[(6-chloro-3-pyridinyl)methyl]-2-imidazolidine and 1-[(6-chloro-3-pyridinyl)methyl]-2-iminothiazole. Methods of using the novel m-nAChR modulators are also provided, including methods of using the compounds as m-nAChR probes and as therapeutic agents to treat mammalian individuals suffering from conditions, disorders or diseases that are responsive to administration of an m-nAChR modulator. The compounds are useful in treating (1) CNS disorders such as Alzheimer's disease, AIDS-associated dementia, Tourette's Syndrome, attention deficit disorder, and attention deficit disorder, (2) inflammation and inflammatory diseases, (3) conditions caused by or associated with smooth muscle contractions, and (4) withdrawal symptoms associated with cessation of chemical substance abuse. The compounds are also useful as non-opiate analgesics, to treat mild, moderate or severe pain. Pharmaceutical formulations containing an m-nAChR modulator of the invention are provided as well.

14 Claims, No Drawings

SUBSTITUTED PYRIDINES AS MODULATORS OF THE MAMMALIAN NEURONAL NICOTINIC ACETYLCHOLINE RECEPTOR

CROSS-REFERENCE TO RELATED APPLICATIONS

This application claims priority to provisional U.S. patent application Ser. No. 60/147,630, entitled "Substituted Pyridines as Modulators of the Mammalian Neuronal Nicotinic Acetylcholine Receptor," filed Aug. 6, 1999.

ACKNOWLEDGEMENT OF GOVERNMENT SUPPORT

This invention was made with Government support under Contract Nos. ES00049 and ES08424 awarded by the National Institutes of Health. The Government has certain rights to this invention.

TECHNICAL FIELD

The present invention relates generally to modulation of the neuronal nicotinic acetylcholine receptor (nAChR). More particularly, the invention relates to novel heterocyclic compounds, specifically substituted pyridine compounds, as modulators of the mammalian nAChR (m-nAChR). The invention additionally relates to methods for synthesizing the novel compounds, to methods for using the novel compounds to modulate the m-nAChR, and to pharmaceutical formulations containing an m-nAChR modulator of the invention as a therapeutic agent.

BACKGROUND

There are a myriad of neurotransmitters and neurotransmitter receptors, each influencing a specific activity within an organism. One type of neurotransmitter receptor is the nAChR, which in humans is found throughout the nervous system in healthy individuals. The nAChR is an acetylcholine receptor that can bind to nicotine and its analogs (i.e., nicotinic agonists). The receptor is known to perform critical functions in humans and is involved in several central nervous system (CNS) disorders, including Alzheimer's disease, AIDS-associated dementia, Tourette's syndrome, cognitive dysfunction (e.g., disorders of attention, focus and concentration, such as "Attention Deficit Disorder" (ADD) and "Attention Deficit Hyperactivity Disorder" (ADHD)) and possibly Parkinson's disease; see, e.g., Halladay et al. (1997) *J. Med. Chem.* 40:4169–4194, U.S. Pat. No. 5,736,560 to Cosford et al., and U.S. Pat. No. 5,922,723 to Bencherif et al.

When nicotine itself is administered into the human blood stream, both central and peripheral effects of nicotine are seen such as fever, increased heart rate, trembling, nausea, increased blood pressure and convulsions, even when the drug is administered in relatively small amounts; nicotine can in fact be fatal when taken orally at doses of 250–350 mg. However, it has been suggested that certain nicotine analogs may, by contrast, be beneficial in the treatment of many diseases (Lin et al. (1994) *J. Med Chem.* 37:3542). That is, it has been proposed that certain nicotinic agents could modulate the nAChR as desired, but without significantly affecting those receptors that have the potential to induce undesirable side effects.

The 6-chloro-3-pyridinyl moiety has been found to confer high potency to several types of compounds acting at the nAChR, resulting in selective antinociceptive or non-opiate analgesic effects. See, for example, Badio et al. (1994) *Mol. Pharmacol.* 45:563–569, and Houghtling et al. (1995) *Mol. Pharmacol.* 48:280–287. This moiety can also confer insecticidal activity, as in the case of imidacloprid, a compound that acts selectively at the insect versus the mammalian nAChR (Kagabu et al. (1997) *Rev. Toxicol.* 1:75–129).

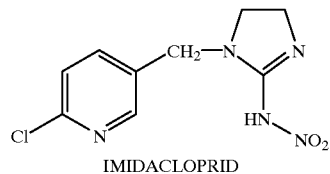

IMIDACLOPRID

Surprisingly, it has been found that the N-desnitro metabolite of imidacloprid, 1-[(6-chloro-3-pyridinyl)methyl]-2-imidazolidine, is selective for the mammalian versus the insect nAChR and is similar in potency to that of (−)-nicotine (Chao et al. (1997) *Pestic. Biochem. Physiol.* 58:77–88).

There remains a need in the art, however, for additional compounds that modulate the nAChR, particularly the mammalian nAChR. Such compounds are useful to treat conditions, diseases and disorders that are responsive to the activity of m-nAChR modulators, including CNS disorders, pain, inflammation and inflammatory diseases, diseases caused by smooth muscle contractions, and withdrawal symptoms associated with cessation of chemical substance abuse.

SUMMARY OF THE INVENTION

In one aspect of the invention, then, novel compounds are provided that are useful as modulators of the m-nAChR. The compounds are substituted pyridines having the general structure of formula (I)

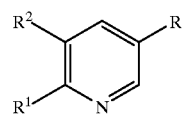

wherein:

R is selected from the group consisting of

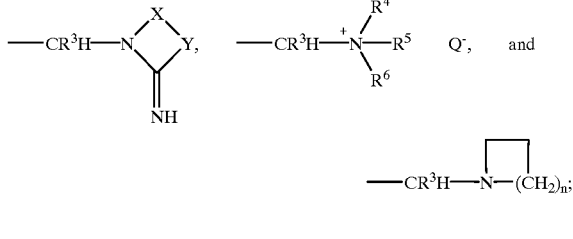

$R^1$ is halo or alkyl;
$R^2$ is selected from the group consisting of hydrogen, alkyl, alkenyl, alkynyl, alkoxy, cyano, halo and nitro;
$R^3$ is hydrogen or alkyl;
$R^4$, $R^5$ and $R^6$ are independently linear, branched or cyclic alkyl;
X is selected from the group consisting of —CHR$^7$=CHR$^8$—, —CR$^7$R$^8$—CR$^9$R$^{10}$—(CR$^{11}$R$^{12}$)$_p$—(CR$^{13}$R$^{14}$)$_q$—, —CR$^7$R$^8$—NH—CR$^9$R$^{10}$—, —CR$^7$R$^8$—N(CH$_3$)—CR$^9$R$^{10}$—, CR$^7$R$^8$—O—

$CR^9R^{10}$— and —$CR^7R^8$—S—$CR^9R^{10}$— wherein $R^7$, $R^8$, $R^9$, $R^{10}$, $R^{11}$, $R^{12}$, $R^{13}$ and $R^{14}$ are independently hydrogen or alkyl and p and q are independently zero or 1;

Y is selected from the group consisting of $CR^{15}R^{16}$, $NR^{17}$, O and S, wherein $R^{15}$ and $R^{16}$ are independently hydrogen or alkyl, and $R^{17}$ is hydrogen, alkyl, alkenyl or alkynyl;

$Q^-$ is an organic or inorganic anion; and n is 1, 2 or 3.

In another aspect of the invention, a method is provided for synthesizing compounds having the structure of formula (I), using compound (II)

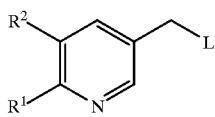

as a starting material. The substituent L is a leaving group that is generally displaceable by a nucleophile, and may be, for example, halo, particularly chloro.

In another aspect of the invention, methods are provided for using compounds having the structure of formula (I) as modulators of the mammalian nAChR receptor. A first method involves contacting the receptor with the compound of formula (I), e.g., in the context of treating a mammalian individual suffering from a condition, disease or disorder that is responsive to administration of an m-nAChR modulator. Such conditions, diseases and disorders include, for example: CNS disorders such as Alzheimer's disease, AIDS-associated dementia, Tourette's syndrome, ADD and ADHD; pain; inflammation and inflammatory diseases; diseases caused by smooth muscle contractions; and withdrawal symptoms associated with the cessation of chemical substance abuse. The compounds are potent in terms of their therapeutic effectiveness, while the occurrence of undesirable side effects is minimal. A second method involves using the novel compounds as nAChR probes, in order to study the function of the nAChR in mammals.

DETAILED DESCRIPTION OF THE INVENTION

Definitions and Nomenclature

Before the present compounds, compositions and methods are disclosed and described, it is to be understood that unless otherwise indicated this invention is not limited to specific molecular structures, synthetic procedures, therapeutic uses, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to use of "a compound of formula (I)" includes use of two or more compounds of formula (I), reference to "a substituent" as in a compound substituted with "a substituent" includes the possibility of substitution with more than one substituent, wherein the substituents may be the same or different.

In this specification and in the claims which follow, reference will be made to a number of terms which shall be defined to have the following meanings:

The term "alkyl" as used herein refers to a branched or unbranched saturated hydrocarbon group of 1 to 8 carbon atoms, such as methyl, ethyl, n-propyl, isopropyl, n-butyl, isobutyl, t-butyl, hexyl, octyl, and the like, as well as cycloalkyl groups of from 3 to 8 carbon atoms, such as cyclopropyl, cyclobutyl, cyclopentyl, cyclohexyl, cycloheptyl and cyclooctyl.

The term "alkenyl" as used herein refers to a branched, unbranched or cyclic hydrocarbon group of 2 to 8 carbon atoms containing at least one double bond, such as ethenyl, n-propenyl, isopropenyl, n-butenyl, isobutenyl, octenyl, and the like. The specific term "cycloalkenyl" intends a cyclic alkenyl group of three to eight, preferably five or six, carbon atoms.

The term "alkynyl" as used herein refers to a branched, unbranched or cyclic hydrocarbon group of 2 to 8 carbon atoms containing at least one triple bond, such as ethynyl, n-propynyl, isopropynyl, n-butynyl, isobutynyl, octynyl, and the like.

The termr "alkylene" as used herein refers to a difunctional branched or unbranched saturated hydrocarbon group of 1 to 8 carbon atoms, such as methylene, ethylene, n-propylene, n-butylene, n-hexylene, octylene, and the like.

The term "alkenylene" as used herein refers to a difinctional branched or unbranched hydrocarbon group of 2 to 8 carbon atoms containing at least one double bond, such as ethenylene, n-propenylene, n-butenylene, n-hexenylene, and the like.

The term "alkoxy" as used herein intends an alkyl group bound through a single, terminal ether linkage; that is, an "alkoxy" group is defined as —O—alkyl where alkyl is as defined above.

The term "heterocyclic" refers to a four-, five- or six-membered monocyclic structure or to an eight- to eleven-membered bicyclic heterocycle; generally, as used herein, the term refers to a monocyclic structure. Each heterocycle consists of carbon atoms and from one to three, typically one or two, heteroatoms selected from the group consisting of nitrogen, oxygen and sulfur, wherein at least one of the heteroatoms is nitrogen.

The term "halo" or "halogen" is used in its conventional sense to refer to a chloro, bromo, fluoro or iodo substituent.

The term "hydrocarbyl" is used in its conventional sense to refer to a hydrocarbon group containing carbon and hydrogen, and may be aliphatic or alicyclic, or may contain a combination of aliphatic and alicyclic moieties. Aliphatic and alicyclic hydrocarbyl groups may be saturated or they may contain one or more unsaturated bonds, typically double bonds. The hydrocarbyl substituents herein generally contain 1 to 8 carbon atoms, and may be substituted with various substituents and finctional groups, or may be modified so as to contain ether and/or thioether linkages. The term "hydrocarbylene" refers to a difinctional hydrocarbyl group, i.e., a hydrocarbyl group that is bound to two distinct molecular moieties.

The term "substituent" as used herein refers to a functional group or nonhydrogen substituent bound to an atom of a molecular moiety herein. Those skilled in the art will appreciate that the compounds and molecular segments drawn and defined herein may be unsubstituted, substituted as specifically indicated, or substituted with other substituents. Examples of substituents which may be present in the compounds of the invention include, but are not limited to, halo, particularly chloro; hydroxy; alkoxy, such as methoxy, n-propoxy and t-butoxy; primary amino ($NH_2$); secondary amino, typically alkyl-substituted amino; tertiary amino, typically alkyl-disubstituted amino; nitro; acyloxy, which may be represented as R'COO—; acylamido, which may be represented as R'CONH— and thio analogs thereof (R'CSO— and R'CSNH—, respectively), wherein R' is alkyl; carboxy (—C(O)OH); alkoxycarbonyl (—C(O)OR'); carbamyl (—C(O)NH$_2$); alkylcarbamyl (C(O)NHR'); alkylsulfonyl (R'SO$_2$—); and alkylphosphonyl (R'P(O)OR'O—). The terms "alkyl," "alkenyl," "hydrocarbyl," etc. as used herein are intended to encompass not only unsubstituted groups but substituted groups containing one or more "substituents" as just defined.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

By the term "effective amount" of a compound as provided herein is meant at least a sufficient amount of the compound to provide the desired effect. A "therapeutically effective amount" of a compound herein, used to treat a mammalian individual suffering from a condition, disorder or disease that is responsive to administration of an m-nAChR modulator, is an amount that is nontoxic but sufficient to provide the desired therapeutic effect. The exact amount required will vary from subject to subject, depending on the species, age, and general condition of the subject, the severity of the condition being treated, and the particular m-nAChR modulator and mode of administration, and the like. Thus, it is not possible to specify an exact "therapeutically effective amount." However, an appropriate "therapeutically effective" amount in any individual case may be determined by one of ordinary skill in the art using only routine experimentation.

By "pharmaceutically acceptable carrier" is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmaceutically acceptable" salt or ester of a novel compound as provided herein is a salt or ester which is not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. Thus, for example, the present method of "treating" a disorder that is responsive to an m-nAChR modulator, as the term "treating" is used herein, encompasses both prevention of the disorder in a predisposed mammalian individual and treatment of the disorder in a clinically symptomatic individual.

The term "modulator" as used herein refers to a compound that alters the activity of the nAChR so that the activity of the nAChR is different in the presence of the compound than in the absence of the compound. "Modulators" include agonists, i.e., compounds that activate nAChR function, partial agonists, and antagonists, compounds that interfere with receptor function. Antagonists include competitive and noncompetitive antagonists, wherein a "competitive antagonist" blocks the receptor site that is specific for the agonist, while "noncompetitive antagonists" inactivate the functioning of the receptor by interacting with a site other than the site that binds the agonist.

The Novel Compounds

The invention provides novel compounds useful as modulators of the m-nAChR, the compounds having the structure of formula (I)

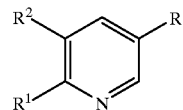

wherein:

R is selected from the group consisting of

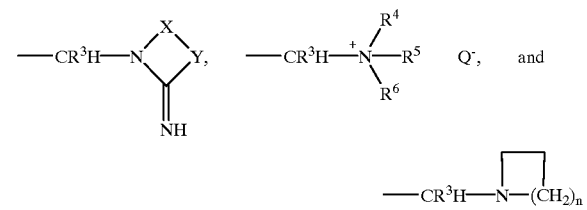

in which $R^1$, $R^2$, $R^3$, $R^4$, $R^5$, $R^6$, X, Y, Q$^-$ and n are as defined earlier herein. Within the aforementioned group, preferred compounds are wherein $R^1$ is halo, particularly chloro, and $R^2$ and $R^3$ are hydrogen; that is, preferred compounds have the structures of formulae (III), (IV) and (V)

(III)

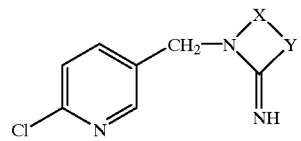

(IV)

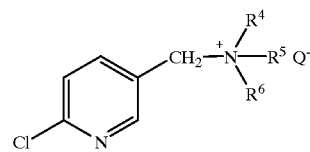

(V)

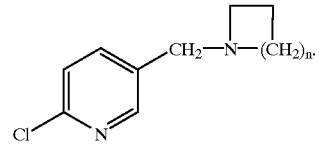

For compounds of formula (III), the various substituents may be more particularly defined as follows:

The linkage X is selected from the group consisting of —CHR$^7$=CHR$^8$—, —CR$^7$R$^8$—CR$^9$R$^{10}$—(CR$^{11}$R$^{12}$)$_m$— (CR$^{13}$R$^{14}$)$_n$—, —CR$^7$R$^8$—NH—CR$^9$R$^{10}$—, —CR$^7$R$^8$—N (CH$_3$)—CR$^9$R$^{10}$—, —CR$^7$R$^8$—O—CR$^9$R$^{10}$— and —CR$^7$R$^8$—S—CR$^9$R$^{10}$— wherein R$^7$, R$^8$, R$^9$, R$^{10}$, R$^{11}$, R$^{12}$, R$^{13}$ and R$^{14}$ are independently hydrogen or alkyl, and m and n are independently zero or 1. Preferred X linkages include —(CH$_2$)$_2$—, —(CH$_2$)$_3$—, —(CH$_2$)$_4$—, —CH=CH—, —CH$_2$—CH(CH$_3$)—, —CH$_2$—CH ($C_2H_5$)—, —CH($CH_3$)—$CH_2$—, —CH($C_2H_5$)—$CH_2$—, —$CH_2$—O—$CH_2$—, —$CH_2$—S—$CH_2$—, —$CH_2$—NH—$CH_2$—, —$CH_2$—N($CH_3$)—$CH_2$—, and particularly preferred linkages are —($CH_2$)$_2$—, —($CH_2$)$_3$— and —CH=CH—.

Y is selected from the group consisting of $CR^{15}R^{16}$, $NR^{17}$, O and S, wherein $R^{15}$ and $R^{16}$ are independently hydrogen or alkyl, preferably hydrogen, and $R^{17}$ is hydrogen, alkyl, alkenyl or alkynyl, preferably hydrogen or alkyl, more preferably hydrogen.

For compounds of formula (IV), $R^4$, $R^5$ and $R^6$ are alkyl, and may be the same or different. The substituents may be branched, linear or cyclic, and are typically either $C_1$–$C_5$ linear alkyl, $C_3$–$C_6$ branched alkyl, or $C_3$–$C_6$ cycloalkyl. Preferred $R^4$, $R^5$ and $R^6$ groups are methyl and ethyl, and it is particularly preferred that all three substituents be methyl or that all three substituents be ethyl. $Q^-$ is an organic or inorganic anion, such as will be formed upon association with an organic or inorganic acid, e.g., hydrochloric, hydrobromic, sulfuric, phosphoric, acetic, citric, and the like.

For compounds of formula (V), the subscript "n" is 1, 2 or 3, such that the nitrogen-containing ring is azetidine, pyrrolidine or piperidine, respectively.

Specific examples of preferred compounds encompassed by structural formula (I) include, but are not limited to, the following:

1:

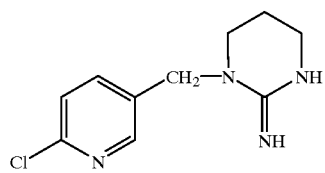

2:

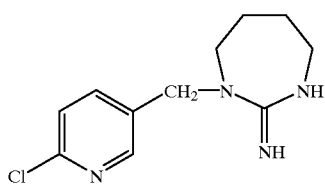

3:

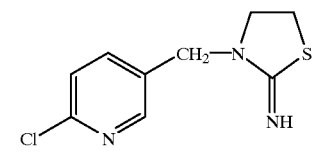

4:

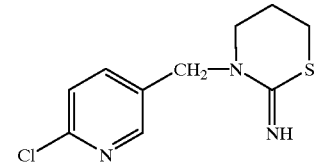

5:

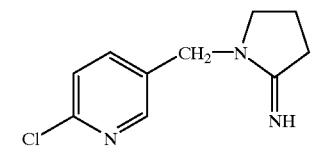

-continued

6:

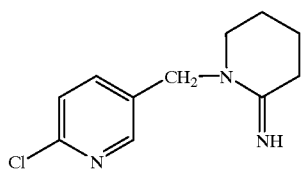

7:

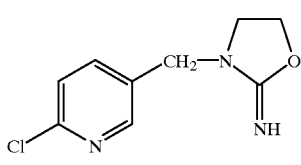

8:

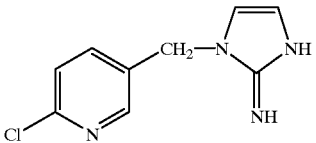

9:

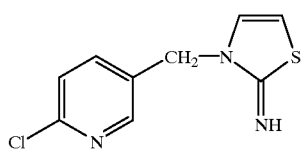

10:

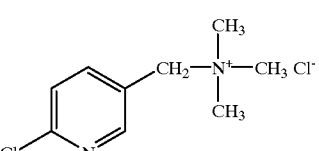

11:

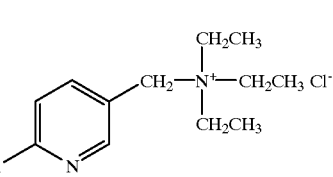

12:

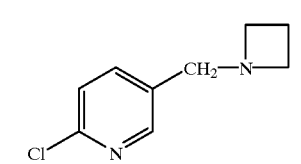

13:

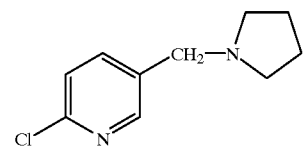

14:

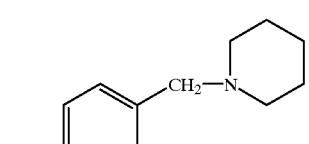

Any of the compounds of the invention, including compounds of formulae (III) and (IV), may be in the form of a salt, typically in the form of an acid addition salt wherein a nitrogen atom within the molecular structure is complexed with a suitable acid. Such salts can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base.

The compounds of the invention may be modified in other ways as well, as will be appreciated by those skilled in the art. Suitable modifications are described, for example, in Latli et al. (1999) *J. Med. Chem.* 42:2227–2234, which discloses various analogs of 1-[(6-chloro-3-pyridinyl)methyl]-2-imidazolidine, and in U.S. Pat. No. 4,742,060 to Shiokawa et al., pertaining to imidacloprid and analogs thereof.

Synthetic Methods

The compounds of the invention are generally prepared using a starting material having the structural formula (II)

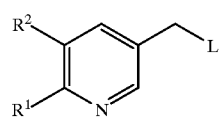

(II)

The substituent L is a leaving group that is generally displaceable by a nucleophile, and may be, for example, halo, particularly chloro. An exemplary starting material is 6-chloro-3-chloromethylpyridine (CCMP)

CCMP wherein nucleophilic attack by an amine moiety, e.g., as may be contained within a diamine $H_2N$—X—$NH_2$. CCMP may be obtained commercially or prepared using synthetic methods known to those skilled in the art and described in the literature (e.g., by Tilley et al. (1979) *J. Heterocyclic Chem.* 16:333–337; Latli et al., *J. Labelled Compds. Radiopharm.* 31:609–613). Typically, reaction progress may be monitored by thin layer chromatography (TLC). If desired, intermediates and products may be purified by chromatography on silica gel and/or recrystallization, and their structures may be confirmed by NMR and mass spectroscopy.

A. Synthesizing Compounds of Formula (III):

Several methods may be used to prepare compounds having the structure of formula (III)

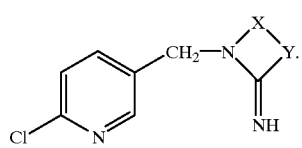

(III)

One suitable method is shown in Scheme 1, which illustrates a two-step reaction in which: (1) a diamine $H_2N$—X—$NH_2$ (wherein X is as defined earlier herein) is coupled to CCMP in a solvent such as acetonitrile, in the presence of an aqueous base such as sodium hydroxide or potassium hydroxide, at room temperature; and (2) the resulting product is then reacted under anhydrous conditions with cyanogen bromide in a solvent such as acetonitrile, toluene or dimethyl formamide.

SCHEME 1

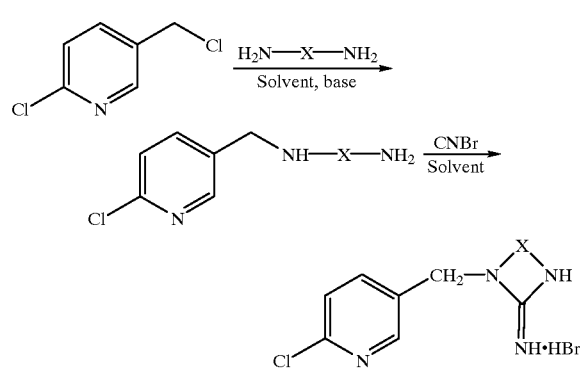

Alternatively, commercially available amine-substituted azoles can be coupled directly to CCMP by refluxing in an appropriate solvent such as ethanol or 2-propanol, as illustrated in Scheme 2:

SCHEME 2

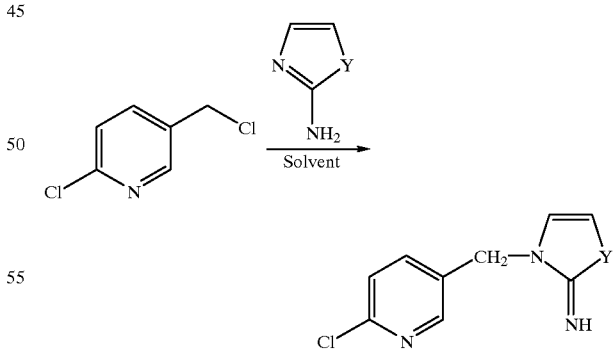

The moiety "Y" in Scheme 2 is as defined earlier herein. In another method, illustrated in Scheme 3, CCMP is coupled to an appropriate haloamine $H_2N$—X—Q in the presence of a base such as triethylamine or potassium carbonate; again, X and Q are as defined above. The product may then be reacted with potassium thiocyanate in a solvent mixture, e.g., of acetonitrile and water, to give the desired product.

SCHEME 3

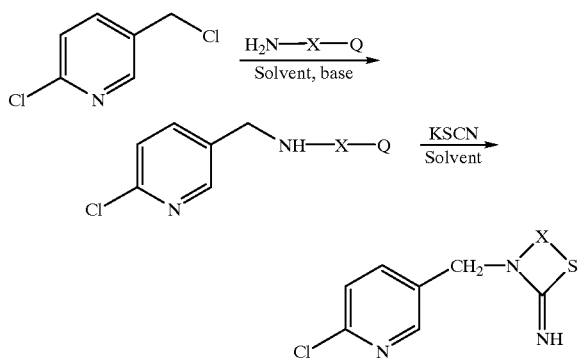

In another method, cyclic amides are first prepared by treating CCMP with a base such as NaH in a solvent such as dimethyl formamide at a low temperature. The resulting carbonyl, as shown in Scheme 4, is then converted to a thiocarbonyl with $P_4S_{10}$ and treated with methyl iodide in a solvent such as ethanol to form a salt. The imine moiety may then be produced by treatment with ammonia in a solvent such as ethanol.

SCHEME 4

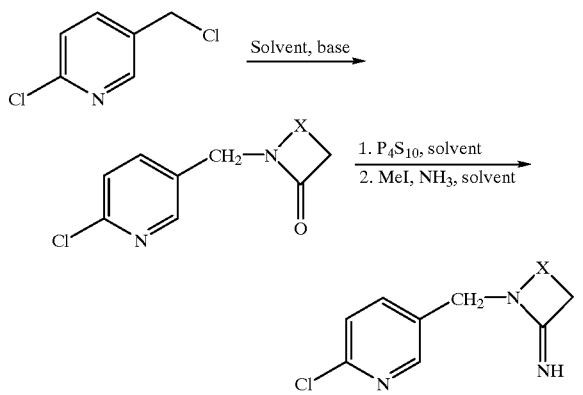

B. Synthesizing Compounds of Formula (IV):

Compounds having the structure of formula (IV)

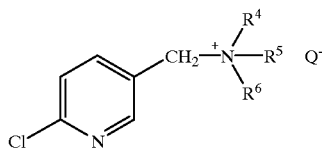

(IV)

may be synthesized from CCMP by treatment with a tertiary amine in an appropriate solvent such as ethanol or 2-propanol, under reflux conditions, as illustrated in Scheme 5.

SCHEME 5

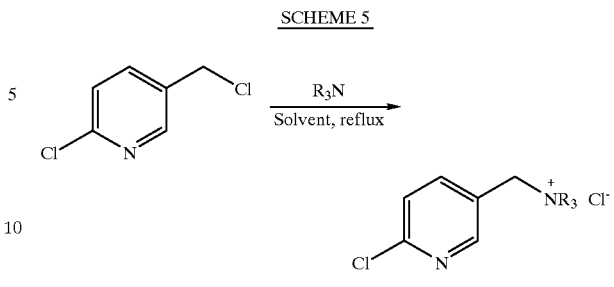

C. Synthesizing Compounds of Formula (V):

Compounds having the structure of formula (V)

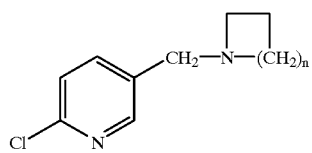

(V)

can be prepared by reacting CCMP with a haloamine $H_2N-(CH_2)_n-Q$ (wherein, as above, n is 1, 2 or 3 and Q is halo) in a solvent such as acetonitrile or methanol, in the presence of an inorganic base such as sodium hydroxide, potassium hydroxide, sodium carbonate or potassium carbonate. The resulting product may then be refluxed in a solvent such as acetonitrile or methanol to form the cyclic amine.

Utility

The compounds of the present invention are useful as probes to study the role of the nAChR generally and the m-nAChR in particular. By comparing the various nicotinic agents of the invention in terms of structure and binding affinity, it is possible to better understand the nature of the m-nAChR itself. The compounds are also useful as starting materials and intermediates in the synthesis of a variety of substituted pyridine derivatives useful as nicotinic agents.

Furthermore, the compounds of the present invention serve as modulators of the m-nAChR and thus are useful as therapeutic agents for treating a mammalian individual suffering from a condition, disease or disorder that is responsive to administration of an m-nAChR modulator. Those with ordinary skill in the art will readily recognize those conditions, diseases and disorders which may be responsive to such administration. The condition, disease or disorder that is responsive to administration of an m-nAChR modulator may be, for example, a CNS disorder. CNS disorders that may be treated with the m-nAChR modulators of the invention include, but are not limited to, Alzheimer's disease, AIDS-associated dementia, Tourette's Syndrome, ADD, ADHD, and possibly Parkinson's disease. Other conditions, disorders and diseases that can be treated using the present compounds include inflammation and inflammatory diseases, e.g., inflammatory skin conditions and inflammatory bowel disease; conditions caused by or associated with smooth muscle contractions, e.g., convulsive disorders, tardive dyskinesia, premature labor, and the like; and withdrawal symptoms associated with cessation of chemical substance abuse, e.g., cessation of opioid use or alcohol abuse.

The compounds of the invention are also useful as non-opiate analgesic agents, to treat pain, including chronic, acute and recurrent pain, postoperative pain, migraine pain, etc. In contrast to NSAIDs (nonsteroidal anti-inflammatory drugs), which are useful for treating only mild or moderate pain, the present compounds are useful to relieve moderate to severe pain. The compounds of the invention may also be contrasted with opiate analgesics, which although effective to treat moderate to severe pain, have well-known side effects including chemical dependence and abuse potential as well as a depressive effect on the respiratory and gastrointestinal system. The m-nAChR modulators of the invention are not opiates, and do not elicit opioid-like withdrawal symptoms or result in physical dependence.

The m-nAChR modulators of the invention may be conveniently formulated into pharmaceutical compositions composed of one or more of the compounds in association with a pharmaceutically acceptable carrier. See *Remington: The Science and Practice of Pharmacy*, 19th Ed. (Easton, Pa.: Mack Publishing Co., 1995), which discloses typical carriers and conventional methods of preparing pharmaceutical compositions that may be used as described or modified to prepare pharmaceutical formulations containing the compounds of the invention.

The compounds may be administered orally, parenterally, transdermally, rectally, nasally, buccally, vaginally or via an implanted reservoir, in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician. Generally, however, dosage will be in the range of approximately 0.001 mg/kg/day to 100 mg/kg/day, more preferably in the range of about 0.1 mg/kg/day to 20 mg/kg/day.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected active agent in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution, emulsion or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

The pharmaceutical compositions of the invention may also include one or more additional active agents, i.e., compounds other than those disclosed and claimed herein, particularly active agents useful for treating CNS disorders.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for.

Silica gel TLC for analysis was performed with precoated plastic sheets with fluorescent indicator; all $R_f$ values reported were for development with 10% methanol/chloroform. Preparative TLC utilized precoated silica gel GF plates. NMR spectra were recorded for $CDCl_3$ or $CD_3OD$ solutions with a Bruker AM-300 spectrometer. Chemical shifts ($\delta$ in ppm) are reported for $^1H$ at 300 MHZ and for $^{13}C$ at 75 MHZ relative to internal tetramethylsilane and $CDCl_3$, respectively. Mass spectra were acquired by GC/MS with a Hewlett-Packard 5971A or 5985B instrument in the electron impact (EI) mode (70 eV, 200° C.). Fast atom bombardment (FAB)-MS (both low and high resolution, LR and HR, respectively) was conducted with a Fisons ZAB2-EQ spectrometer. Melting points recorded on a Fisher-Johns apparatus are uncorrected. Reagents were obtained from Aldrich Chemical Co. (Milwaukee, Wis.), except for EDTA and (−)-nicotine (tartrate salt), which were obtained from Sigma Chemical Co. (St. Louis, Mo.), and 2-chloroethylamine HCl from Lancaster (Windham, N.H.). Solvents were reagent or HPLC grade. [N-methyl-$^3H$](−)-Nicotine ([$^3H$]-nicotine) at 78 Ci/mmol was purchased from DuPont NEN Research Products (Boston, Mass.). Each compound was >98% pure based on TLC and $^1H$ and $^{13}C$ NMR integrations.

EXAMPLE 1

(a) 1-(6-Chloro-3-pyridinyl)methyl-1,3-diaminopropane:

CCMP (1.62 g, 10.0 mmol) in $CH_3CN$ (15.0 mnL) was added dropwise to a solution of 1,3-diaminopropane (0.835 mL, 10.0 mmol) in $CH_3CN$ (20.0 mL) in a 2 hr period at room temperature. The resulting mixture was stirred overnight. A 30% aqueous solution of NaOH (2.0 mL) was added and the mixture was concentrated in vacuo. The residue was extracted with $CHCl_3$, dried ($MgSO_4$), filtered and concentrated under reduced pressure to give 1.87 g of a viscous oil. Purification by preparative TLC gave 0.86 g of a bis-derivative ($R_f$=0.4 in 10% $CH_3OH/CHCl_3$) and 0.35 g of the desired product, $R_f$=0.16 in 10% $CH_3OH/CHCl_3$. $^1H$ NMR ($CDCl_3$) $\delta$: 8.32(d, J=2.1 Hz, 1H), 7.6(dd, J=2.1, 8.1 Hz, 1H), 7.25(d, J=8.1 Hz, 1H), 3.78(s, 2H), 3.43(s, exch. 1H), 2.78(t, J=6.8 Hz, 2H), 2.68(t, J=6.8 Hz, 2H), 1,78(br s, exch. 2H), 1.65(q, J=6.8 Hz, 2H). $^{13}C$ NMR ($CDCl_3$) $\delta$: 151.13, 148.89, 138.8, 129.42, 124.70, 50.48, 45.88, 38.21, 20.56.

(b) 1-(6-Chloro-3-pyridinyl)methyl-2-iminotetrahydropyrimidine (1):

The monoalkylated diamine prepared in part (a) (144.0 mg, 0.72 mmol) was dissolved in $CH_3CN$ (5.0 mL) and added dropwise to a solution of CNBr (80.0 mg, 0.75 mmol) in $CH_3CN$ (3.0 mL) at room temperature. The mixture was stirred overnight. The resulting precipitate was filtered off and washed with $CH_3CN$ (3×10 mL). The solid was dried under reduced pressure to give 70 mg (32% yield) of the product 1, mp=220° C., $^1$H NMR ($CDCl_3$) δ: 8.66(d, J=2.2 Hz, 1H), 8.16(dd, J=2.2, 8.3 Hz, 1H), 7.57(d, J=8.3 Hz, 1H), 4.42(s, 2H), 3.32(t, J=7.7 Hz, 2H), 3.15(t, J=7.7 Hz, 2H), 2.22(q, J=7.7 Hz, 2H). $^{13}$C NMR ($CDCl_3$) δ: 163.21, 153.93, 152.89, 143.24, 128.27, 126.31, 48.31, 46.18, 38.16, 25.49. FAB-LR: $MH^+$(225, 45%), $MH^+$+2(15%), 200(100%), 202 (33%). FAB-HR: $C_{10}H_{13}ClN_4H^+$, calc. 225.090699, found 225.090950.

EXAMPLE 2

(a) 1-[(6-Chloro-3-pyridinyl)methyl]-1,4-diaminobutane:

CCMP (324 mg, 2.0 mmol) was added in $CH_3CN$ (10 mL) over a period of 2 h to a solution of 1,4-diaminobutane (352 mg, 4.0 mmol) in $CH_3CN$ (10 mL) containing triethylamine (0.5 mL), and the resulting mixture was stirred overnight at 25° C. After the workup described in part (a) of Example 1, the desired product was isolated by preparative TLC with 10% $CH_3OH/CHCl_3$ to give 380 mg of the desired product in 89% yield as a yellowish oil, $R_f$=0.13, and 80 mg of 1,4-bis[(6-chloro-3-pyridinyl)methyl]-1,4-diaminobutane as a pale resin, $R_f$=0.40.

(b) 1-[(6-Chloro-3-pyridinyl)methyl]-2-iminotetrahydrodiazepine (2):

The monoalkylated diamine prepared in part (a) (178 mg, 0.83 mmol) in N,N-dimethylformamide (DMF) (5 mL) was added at 25° C. to cyanogen bromide (90 mg, 0.85 mmol) in DMF (2 mL), and the resulting solution was stirred overnight. The product 2 was isolated by concentration in vacuo and then preparative TLC as above to give 46 mg in 53% yield based on the reacting diamine, mp=125° C. $^1$H NMR ($CDCl_3$) δ: 8.31 (d, J=2.1 Hz, 1H), 7.67 (dd, J=2.1, 8.1 Hz, 1H), 7.27 (d, J=8.1 Hz, 1H), 3.78 (s, 2H), 2.70 (t, J=6.5 Hz, 2H), 2.62 (t, J=6.5 Hz, 2H), 2.05 (m, 3H, exch), 1.51 (m, 4H). $^{13}$C NMR ($CDCl_3$) δ: 149.63, 149.01, 138.44, 134.72, 123.67, 50.13, 48.91, 41.60, 30.85, 27.10. FAB-LR: $MH^+$ (239, 100%), $MH^+$+2(32%), 154(40%), 156(11%). FAB-HR: $C_{11}H_{15}ClN_4H^+$, calcd 239.1063, found 239.1059.

EXAMPLE 3

(a) 1-(6-Chloro-3-pyridinyl)methyl-2-chloroethylamine:

A solution of CCMP (1.62 g, 10.0 mmol), 2-chloroethylamine hydrochloride (1.3 g, 11.2 mmol), and triethylamine (1.53 mL, 11.0 mmol) in $CH_3CN$ (20.0 mL) was stirred at room temperature for 40 hr. The mixture was then concentrated in vacuo and the product was isolated by preparative TLC using 10% $CH_3OH/CHCl_3$ to give 1.0 g of the desired product, 70% yield based on reacted CCMP, $R_f$=0.6 in 10% $CH_3OH/CHCl_3$.

(b) 1-($^6$-Chloro-3-pyridinyl)methyl-2-iminothiazolidine (3):

A solution of the amine prepared in part (a) (205.0 mg, 1.0 mmol), and potassium thiocyanate (100.0 mg, 1.0 mmol) in $CH_3CN$ (5.0 mL) and water (5.0 mL) was refluxed for 3 hr. The solution was then concentrated under reduced pressure. The product was isolated by preparative TLC to give 50 mg of the desired compound 3 in 19% yield, mp=190° C. and 62 mg of 1,4-(6-chloro-3-pyridinyl)methyl piperazine. $^1$H NMR ($CDCl_3$) δ: 8.32 (d, J=2.1 Hz, 1H), 7.69 (dd, J=2.1, 8.2 Hz, 1H), 7.31 (d, J=8.2 Hz, 1H), 4.57 (s, 2H), 3.51 (t, J=6.8 Hz, 2H), 3.17 (t, J=6.8 Hz, 2H). $^{13}$C NMR ($CDCl_3$) δ: 164.23, 150.64, 149.10, 138.79, 131.87, 124.26, 51.17, 46.06, 26.89. FAB-LR: $MH^+$(228, 100%), $MH^+$+2(34%). FAB-HR: $C_9H_{10}ClN_3SH^+$, calc. 228.036222, found 228.036550.

EXAMPLE 4

(a) 1-[(6-Chloro-3-pyridinyl)methyl]-3-chloropropylamine:

A solution of CCMP 1.62 g, 10 mmol), 3-chloropropylamine (1.7 g, 13 mmol), and triethylamine (1.8 mL, 13 mmol) in $CH_3CN$ (20 mL) was stirred at 55° C. overnight before it was concentrated under reduced pressure and worked up as described in part (a) of Example 1. Purification by preparative TLC with 10% $CH_3OH/CHCl_3$ gave 1.5 g of a yellowish oil in 68% yield, $R_f$=0.50.

(b) 1-[(6-Chloro-3-pyridinyl)methyl]-2-iminotetrahydrothiazine (4):

A solution of the compound prepared in part (a) (219 mg, 1.0 mmol) and potassium thiocyanate (100 mg, 1.02 mmol) in $CH_3CN$ (5 mL) and water (5 mL) was refluxed overnight. The solution was then treated as described in the preceding examples to give 101 mg of the solid product 4 in 42% yield, mp=215° C. $^1$H NMR ($CDCl_3$ /$CD_3OD$) δ: 8.36 (d, J=2.1 Hz, 1H), 7.78 (dd, J=2.1, 8.2 Hz, 1H), 7.45 (d, J=8.2 Hz, 1H), 4.96 (s, 2H), 3.69 (t, J=6.5 Hz, 2H), 3.31 (t, J=6.5 Hz, 2H), 2.35 (q, J=6.5 Hz, 2H), 1.42 (br s, 4H). $^{13}$C NMR ($CDCl_3$, /$CD_3OD$) δ: 165.84, 151.16, 148.23, 138.52, 127.98, 124.77, 52.76, 49.35, 26.64, 22.51. FAB-LR: $MH^+$ (242, 100%), $MH^+$+2(34%). FAB-HR: $C_{10}H_{12}ClN_3SH^+$, calcd 242.0518, found 242.0518.

EXAMPLE 5

(a) 1-(6-Chloro-3-pyridinyl)methyl-2-pyrrolidinone:

NaH (138.0 mg, 3.0 mmol, 50% oil dispersion) was washed three times with hexane and then suspended in DMF (5.0 mL). To this, a solution of 2-pyrrolidinone (190.0 μL, 2.5 mmol) in DMF (2.0 mL) was added slowly at 0° C. The resulting mixture was further stirred for 1 hr before CCMP (324.0 mg, 2.0 mmol) in DMF (2.0 mL) was added dropwise at this temperature. The mixture was then stirred overnight as the ice melted. The reaction mixture was poured into water and extracted with $CHCl_3$, dried ($MgSO_4$), filtered and concentrated in vacuo. Purification by preparative TLC gave the desired product in 97% yield, $R_f$=0.53 in 10% $CH_3OH/CHCl_3$.

(b) 1-(6-Chloro-3-pyridinyl)methyl-2-pyrrolidinethione:

To a suspension of phosphorous pentasulfide (1.02 g, 2.3 mmol) in dry THF (10.0 mL) was added $Na_2CO_3$ (238.5 mg, 2.25 mmol) at room temperature. The mixture turned to a yellow solution in a few minutes and was further stirred for 30 min. To this solution was added the pyrrolidinone derivative prepared in part (a) (0.4 g, 1.9 mmol) in THF (5.0 mL) and the solution was stirred for 3 hr. A solution of 10% $Na_2HPO_4$ (10 mL) was added and the organic phase was extracted with EtOAc, dried ($MgSO_4$), filtered and concentrated in vacuo. The product was isolated by preparative TLC to give 280 mg in 68% yield, $R_f$=0.6 in 10% $CH_3OH/CHCl_3$.

(c) 1-(6-Chloro-3-pyridinyl)methyl-2-iminopyrrolidine (5):

To a solution of the thione prepared in part (b) (226.5 mg, 1.0 mmol) in acetone (10.0 mL) was added methyl iodide (70.0 μL, 1.1 mmol) at room temperature. The resulting solution was stirred for 48 hr before it was concentrated under reduced pressure. The oil residue was then dissolved in absolute ethanol (10.0 mL) and anhydrous ammonia was bubbled through slowly for 20 min. The reaction flask was then sealed and stirred at room temperature for 48 hr. After concentration in vacuo the compound was isolated by preparative TLC to give the product 5 in 99% yield, $R_f$=0.03 in 10% CH$_3$OH/CHCl$_3$, mp=166° C. $^1$H NMR (CDCl$_3$) δ: 9.08 (br s, 4H), 8.48(d, J=2.3 Hz, 1H), 7.9 (dd, J=2.3, 8.2 Hz, 1H), 7.40 (d, J=8.2 Hz, 1H), 5.08 (s, 2H), 3.67 (t, J=7.2 Hz, 2H), 3.30 (t, J=7.2 Hz, 2H), 2.23 (q, J=7.2 Hz, 2H). $^{13}$C NMR (CDCl$_3$) δ: 168.62, 151.38, 149.14, 139.55, 127.68, 124.76, 53.16, 46.81, 32.01, 18.56. FAB-LR: MH$^+$(210.1, 100%), MH$^+$+2(33%). FAB-HR: C$_{10}$H$_{12}$ClN$_3$H$^+$, calc. 210.0798, found 210.08023.

EXAMPLE 6

(a) 1-[(6-Chloro-3-pyridinyl)methyl]-2-piperidone:

NaH (138 mg, 3.0 mmol, 50% oil dispersion) was washed three times with hexane and then suspended in DMF (5 mL). To this was added a solution of 6-valerolactam (2-piperidone) (0.60 g, 6.0 mmol) in DMF (2 mL) slowly at 0° C. The resulting mixture was further stirred for 1 h before CCMP (0.81 g, 5.0 mmol) in DMF (2 mL) was added dropwise at this temperature. The mixture was then stirred overnight as the ice melted. The reaction mixture was poured into water, extracted with chloroform, dried over MgSO$_4$, filtered, and concentrated in vacuo. Purification by preparative TLC with 10% CH$_3$OH/CHCl$_3$ form gave the desired product as a yellowish oil in 90% yield, R$_f$=0.60.

(b) 1-[(6-Chloro-3-pyridinyl)methyl]-2-thiopiperidone:

To a suspension of P$_4$S$_{10}$ (1.0 g, 2.25 mol) in dry THF (10 mL) was added Na$_2$CO$_3$ (238 mg, 2.25 mmol) at 25° C. The mixture was stirred for 30 min. To this solution was added the piperidone derivative prepared in part (a) (0.4 g, 1.78 mmol) in THF (5 mL), and the solution was stirred at 25° C. for 3 h. A solution of 10% Na$_2$HPO$_4$ (10 mL) was added, and the organic phase was extracted with ethyl acetate, dried (MgSO$_4$), filtered, and concentrated in vacuo. The product was isolated by preparative TLC with 10% CH$_3$OH/CHCl$_3$ to give 280 mg in 65% yield, R$_f$=0.73.

(c) 1-[(6-Chloro-3-pyridinyl)methyl]-2-iminopiperidine (6):

To a solution of the thiopiperidone prepared in part (b) (89 mg, 0.37 mmol) in acetone (5 mL) was added methyl iodide (26 μL, 0.4 mmol) at 25° C. The resulting solution was stirred for 48 h before it was concentrated under reduced pressure. The oil residue was then dissolved in absolute ethanol (10 mL), and anhydrous ammonia was bubbled in slowly for 20 min. The reaction flask was then sealed and stirred at 25° C. for 48 h. After concentration in vacuo the product was isolated by preparative TLC with 10% CH$_3$OH/CHCl$_3$ to give the hygroscopic product 6 in 93% yield, R$_f$=0.03. $^1$H NMR (CDCl$_3$) δ: 8.70 (br s, 4H), 8.42 (d, J=2.1 Hz, 1H), 7.85 (dd, J=2.1, 8.2 Hz, $^1$H), 7.38 (d, J=8.2 Hz, 1H), 5.04 (s, 2H), 3.46 (t, J=5.0 Hz, 2H), 1.91 (m, 4H). $^{13}$C NMR (CDCl$_3$) δ: 165.34, 151.66, 149.19, 139.46, 127.50, 124.90, 52.65, 49.80, 28.71, 21,92, 17.82. FAB-LR: MH$^+$ (224, 100%), MH$^+$+2(38%). FAB-HR: C$_{11}$H$_{14}$ClN$_3$H$^+$, calcd 224.09545, found 15 224.09519.

Example 7

(a) 2-Iminotetrahydrothiazine:

A solution of 3-bromopropylamine HBr (2.19 g, 10 mmol) and potassium thiocyanate (0.972 g, 10 mmol) in water (10 mL) was heated at 90° C. for 3 h. The solution was concentrated under reduced pressure at 25° C. and the semisolid residue extracted with hot ethanol. Anhydrous ether was added to the combined ethanolic solutions to give the product in 96% yield (1.9 g) as a white powder, mp=131° C.

(b) 1-[(6-Chloro-3-pyridinyl)methyl]-2-imino-1,3-oxazolidine (7):

To a suspension of NaH (112 mg, 2.4 mmol, 50% oil dispersion) in DMF (5 mL) was added the compound prepared in part (a) (294 mg, 2.4 mmol) in DMF (2 mL) at 0° C. The mixture was stirred for 1 h; then CCMP (190 mg, 1.73 mmol) was added in dry DMF (8 mL) dropwise. The resulting mixture was stirred overnight as the ice melted. Water (10 mL) was added, and the reaction was extracted with chloroform, dried (MgSO$_4$), filtered, and concentrated in vacuo. The product was isolated by preparative TLC as above to give 130 mg of a hygroscopic material 7 in 52% yield. $^1$H NMR (CDCl$_3$) δ: 8.34 (d, J=2.1 Hz, 1H), 7.74 (dd, J=2.1, 8.2 Hz, 1H), 7.32 (d, J=8.2 Hz, 1H), 4.48 (s, 2H), 4.26 (t, J=7.4 Hz, 2H), 3.36 (t, J=7.4 Hz, 2H). $^{13}$C NMR (CDCl$_3$) δ=160.75, 150.81, 149.07, 138.40, 131.34, 124.29, 63.48, 46.27, 46.12. FAB-LR: MH$^+$ (212, 100%), MH$^+$+2(33%). FAB-HR: C$_9$H$_{10}$ClN$_3$OH$^+$, calcd 212.0591, found 212.0597.

EXAMPLE 8

1-[(6-Chloro-3-pyridinyl)methyl]-2-iminoimidazole (8):

2-Aminoimidazole sulfate (1.0 g, 7.57 mmol) was dissolved in a saturated solution of K$_2$CO$_3$. The solution was then concentrated in vacuo to give a solid residue which was extracted with hot ethanol. The ethanolic solution was then concentrated to give 0.71 g of 2-aminoimidazole as a brownish oil (86% crude yield). The free base (100 mg. 1.2 mmol) and CCMP (162 mg, 1.0 mmol) were dissolved in 2-propanol (10 mL) and refluxed for 40 h. The mixture was then concentrated in vacuo, and the product was isolated by preparative TLC (2.0 mm plate) using 10% CH$_3$OH/CHCl$_3$ as eluent to give 116 mg of the desired compound 8 in 56% yield mp=188° C., R$_f$=0.10. $^1$HNMR (CDCl$_3$) δ: 8.25 (d, J=2.1 Hz, 1H), 7.40 (dd, J=2.1, 8.3 Hz, 1H), 7.30 (d, J=8.3 Hz, 1H), 6.66 (d, J=1.0 Hz, 1H), 6.52 (d, J=1.0 Hz, 1H), 4.93 (s, 2H), 4.20 (br s, exch. 4H). $^{13}$C NMR (CDCl$_3$) δ: 162.88, 151.25, 148.65, 137.51, 130.92, 124.98, 124.58, 115.44, 45.40. MS-FAB-LR; MH$^+$ (209, 100%), MH$^+$30 2(34%). FAB-HR; C$_9$H$_9$ClN$_4$H$^+$, calcd 209.0594, found 209.0593.

EXAMPLE 9

1-(6-Chloro-3-pyridinyl)methyl-2-iminothiazole (9):

A solution of CCMP (230.0 mg, 1.42 mmol) and 2-aminothiazole (156.0 mg, 1.56 mmol) in 2-propanol (6.0 mL) was refluxed for 40 h. The mixture was then cooled down to room temperature and concentrated in vacuo. The solid residue was purified by preparative TLC (2.0 mm plate) using 20% CH$_3$OH/CHCl$_3$ as eluent to give 310 mg of a yellowish solid in 97% yield, recovered by extraction of the TLC silica gel with methanol. mp=205–206° C. $^1$H NMR (CDCl$_3$: CD$_3$OD) δ: 8.42 (d, J=2.1 Hz, 1H), 7.85 (dd, J=2.1, 8.2 Hz, 1H), 7.46 (d, J=8.2 Hz, 1H), 6.37 (d, J=4.7 Hz, 1H), 5.80 (d, J=4.7 Hz, 1H), 4.88 (s, 2H). $^{13}$C NMR (CDCl$_3$: CD$_3$OD) δ: 168.21, 151.24, 148.38, 138.71, 128.73, 128.29, 124.47, 107.07, 47.68, MS-FAB-LR: MH$^+$(226, 100%), MH$^+$+2(228,34%). FAB-HR: C$_9$H$_8$ClN$_3$SH$^+$, calc. 226.020572, found 226.021030.

EXAMPLE 10

1-(6-Chloro-3-pyridinyl)methyl-1,1,1-trimethylammonium chloride (10):

A solution of CCMP (180.0 mg, 1.11 mmol) and trimethylamine (excess, 70% solution in water) in 2-propanol, was refluxed overnight and then concentrated. The product was isolated by silica gel chromatography to give 230 mg of a hygroscopic colorless compound in 93% yield. $^1$H NMR (CDCl$_3$) δ: 8.68 (d, J=2.2 Hz, 1H), 8.20 (dd, J=2.2, 8.1 Hz, 1H), 7.56 (d, J=8.1 Hz, 1H), 4.86 (s, 2H), 3.27 (br s, 9H). $^{13}$C NMR (CDCl$_3$) δ: 153.16, 152.63, 143.05, 124.50, 122.71, 58.80, 51.95. MS-FAB-LR: [M-Cl]$^+$(185, 100%), [M-Cl]$^+$+2(187, 32%). FAB-HR: [M-Cl]$^+$: C$_9$H$_{14}$ClN$_2^+$, calc. 185.084551, found 185.084581.

EXAMPLE 11

1-(6-Chloro-3-pyridinyl)methyl-1,1,1-triethylammonium chloride (11):

As seen before, a solution of CCMP (190.0 mg, 1.185 mmol) and triethylamine (182.0 L, 1.3 mmol) in 2-propanol (10.0 mL) was refluxed overnight. Concentration under reduced pressure followed by preparative TLC purification gave 280 mg of a hygroscopic colorless product in 91% yield. $^1$H NMR (CDCl$_3$) δ: 8.58 (d, J=2.2 Hz, 1H), 8.32 (dd, J=2.2, 8.2 Hz, 1H), 7.26 (d, J=8.2 Hz, 1H), 5.18(s, 2H), 3.34 (q, J=7.1 Hz, 6H), 1.52 (t, J=7.1 Hz, 9H). $^{13}$C NMR (CDCl$_3$) δ: 153.29, 152.36, 142.74, 124.78, 122.42, 57.23, 52.89, 7.43. MS-FAB-LR: [M-Cl]$^+$(227, 100%), [M-Cl]$^+$+2(229, 34%). FAB-HR: [M-Cl]$^+$: C$_{12}$H$_{20}$ClN$_2^+$, calc. 227.131502, found 227.133640.

EXAMPLE 12

1-(6-Chloro-3-pyridinyl)methylazetidine (12):

A solution of 1-(6-chloro-3-pyridinyl)methyl-3-chloropropylamine (219.0 mg, 1.0 mmol), prepared as in Example 4, part (a), was refluxed in CH$_3$CN (5.0 mL) overnight. The product was isolated, after the usual work-up and purification on silica gel, as a pale yellow oil in 60% yield or 110 mg. R$_f$=0.53 in 10% CH$_3$OH/CHCl$_3$. $^1$H NMR (CDCl$_3$) δ: 8.28 (d, J=2.1 Hz, 1H), 7.62 (dd, J=2.1, 8.1 Hz, 1H), 7.24 (d, J=8.1 Hz, 1H), 3.55 (s, 2H), 3.22 (t, J=7.0 Hz, 4H), 2.10 (q, J=7.0 Hz, 2H). $^{13}$C NMR (CDCl$_3$) δ: 149.86, 149.28, 138.78, 132.72, 123.78, 59.81, 54.98, 17.42. MS-FAB-LR: MH$^+$(183, 100%), MH$^+$+2(185, 34%). FAB-HR: C$_9$H$_{11}$ClN$_2$H$^+$, calc. 183.068901, found 183.0648550.

EXAMPLE 13

1-($^6$-Chloro-3-pyridinyl)methylpyrrolidine (13):

CCMP (162.0 mg, 1.0 mmol), pyrrolidine (167.0 μL, 2.0 mmol), and K$_2$CO$_3$ (138.0 mg, 1.0 mmol) in CH$_3$CN (10.0 mL) were refluxed overnight. The mixture was cooled down to room temperature and water was added. Extraction with CHCl$_3$, drying (MgSO$_4$), filtration and concentration in vacuo gave a residue which was purified by preparative TLC using 10% CH$_3$OH/CHCl$_3$ as eluent to give a yellowish oil in 96% yield. R$_f$=0.56 in 10% CH$_3$OH/CHCl$_3$. $^1$H NMR (CDCl$_3$) δ: 8.31(d, J=2.2 Hz, 1H), 7.66 (dd, J=2.2, 8.1 Hz, 1H), 7.28 (d, J=8.1 Hz, 1H), 3.60 (s, 2H), 2.49 (t, J=6.5 Hz, 4H), 1.79 (q, J=6.5 Hz, 4H). $^{13}$C NMR (CDCl$_3$) δ: 149.95, 149.69, 139.21, 133.95, 123.82, 56.87, 54.02, 23.48. MS-FAB-LR: MH$^+$(197, 100%), MH$^+$+2(199, 27%). FAB-HR: C$_{10}$H$_{13}$ClN$_2$H$^+$, calc. 197.084551, found 197.084630.

EXAMPLE 14

1-($^6$-Chloro-3-pyridinyl)methylpiperidine (14):

The procedure of Example 15 was used to prepare this compound from CCMP (162 mg, 1.0 mmol), piperidine (200 μL, 2.0 mmol), and K$_2$CO$_3$ (138 mg, 1.0 mmol) in CH$_3$CN (10 mL) to give 180 mg after silica gel purification in 85% yield as a yellow oil which solidified upon standing at 25° C., mp=48° C., R$_f$=0.60. $^1$H NMR (CDCl$_3$) δ=8.28 (d, J=2.2 Hz, 1H), 7.65 (dd, J=2.2, 8.1 Hz, 1H), 7.27 (d, J=8.1 Hz, 1H), 3.44 (s, 2H), 2.36 (t, J=6.0 Hz, 4H), 1.56 (q, J=6.0 Hz, 4H), 1.43 (m, 2H). $^{13}$C NMR (CDCl$_3$) δ: 149.91, 149.80, 139.25, 133.20, 123.60, 59.78, 54.21, 25.72, 24.18. MS-FAB-LR: MH$^+$ (211, 100%), MH$^+$+2(30%), 154(74%), 156(22%). FAB-HR: C$_{11}$H$_{15}$ClN$_3$H$^+$, calcd 211.10, found 211.1005. The identity of the product was further confirmed using elemental analysis.

EXAMPLE 15

Biological Evaluation

Representative compounds of the invention were investigated by way of the experimental protocol described below. The test results are reported in Table 1.

Production of recombinant α4β2 nAChR:

Recombinant baculovirus stocks containing inserts for the rat α4 and β2 nAChR subunits were independently amplified as described by Wang et al. (1996) *J. Neurosci. Res.* 44:350–354. Production of the α4β2 nAChR was achieved by infection of Sf9 insect cells with each recombinant viral stock. Cells were harvested 48–72 h post infection by centrifugation for 10 min at 100 g, then washed in a phosphate-buffered saline, and homogenized in a small volume of buffer (20 mM Tris-HCl, pH 7.4, 118 mM NaCl, 4.8 M KCl, 2.5 mM CaCl$_2$, 1.2 mM MgSO$_4$, and 1.0 mM EDTA), followed by centrifugation for 10 min at 300 g. The final step was centrifugation of the supernatant at 37000 g. The membrane pellet was resuspended in buffer and adjusted to 20 mg of total protein per 100 mL. These nAChR preparations were used immediately for binding assays or stored as single experiment aliquots at −80° C.

Binding Assays:

The standard assay involved incubation of 1 nM [$^3$H] nicotine and various concentrations of inhibitor with 20 μg α4β2 nAChR preparation in 0.25 mL buffer for 30 min at 22° C. Reactions were terminated by addition of 3 mL ice-cold 0.9% NaCl followed by rapid vacuum filtration through filtermat B glass fiber filters and two 3-mL washes on the filter. Filters were pre-soaked at least 60 min in 0.1% w/v polyethyleneimine to reduce non-specific binding. Specific binding was defined as total binding with radioligand alone minus non-specific binding determined with 1 mM of nicotine. The concentration of test compounds for 50% inhibition (IC$_{50}$) was determined by iterative non-linear least-squares regression using the SigmaPlot program (Jandel Scientific Software, San Rafael, Calif.). The data reported are means±standard deviations with four determinations or are individual values for two determinations.

TABLE 1

| Compound, R = | Inhibition of [$^3$H](−)-nicotine binding to α4β2 nAChR) IC$_{50}$ (nM) |
|---|---|
| 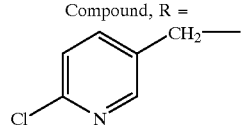 (1) | 58, 63 |
| 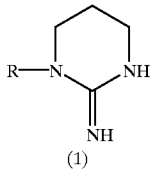 (2) | 2.8 ± 1.0 |
| 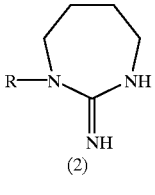 (3) | 2.3 ± 0.3 |

TABLE 1-continued

| Compound, R = 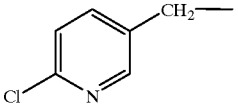 | Inhibition of [³H](−)-nicotine binding to α4β2 nAChR) IC$_{50}$ (nM) |
|---|---|
| 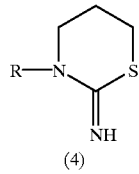 (4) | 14 ± 4 |
| 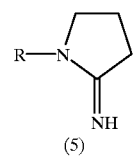 (5) | 3.5 ± 0.7 |
| 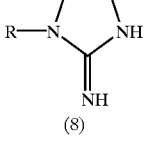 (6) | 11 ± 5 |
| 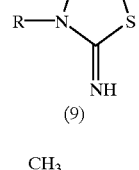 (7) | 7.2 ± 2.0 |
| 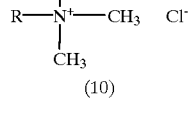 (8) | 23 ± 9 |
| 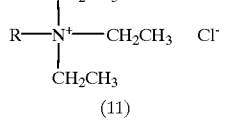 (9) | 0.91 ± 0.40 |
|  (10) | 16, 20 |
| 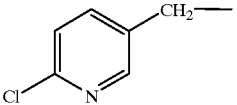 (11) | 2400, 3700 |
| 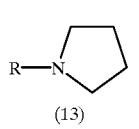 (12) | 16 ± 14 |

TABLE 1-continued

| Compound, R = 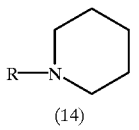 | Inhibition of [³H](−)-nicotine binding to α4β2 nAChR) IC$_{50}$ (nM) |
|---|---|
| 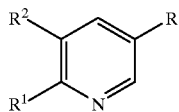 (13) | 8.8 ± 2.8 |
| 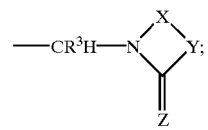 (14) | 14 ± 3 |

What is claimed is:

1. A compound having the structural formula (I)

$$\begin{array}{c}R^2\quad\quad R\\ \diagdown\quad\diagup\\ \text{pyridine}\\ \diagup\\ R^1\end{array}$$

wherein:

R has the structure $$-CR^3H-N\begin{array}{c}X\\ \diagdown\\ \diagup\\ Z\end{array}Y;$$

$R^1$ is halo or $C_1$–$C_8$ alkyl;

$R^2$ is selected from the group consisting of hydrogen, $C_1$–$C_8$ alkyl, $C_2$–$C_8$ alkenyl, $C_2$–$C_8$ alkynyl, $C_1$–$C_8$ alkoxy, cyano, halo and nitro;

$R^3$ is hydrogen or $C_1$–$C_8$ alkyl;

X is selected from the group consisting of —CHR$^7$=CHR$^8$—, —CR$^7$R$^8$—CR$^9$R$^{10}$—(CR$^{11}$R$^{12}$)$_p$—(CR$^{13}$R$^{14}$)$_q$—, —CR$^7$R$^8$—NH—CR$^9$R$^{10}$—, —CR$^7$R$^8$—N(CH$_3$)—CR$^9$R$^{10}$—, —CR$^7$R$^8$—O—CR$^9$R$^{10}$— and —CR$^7$R$^8$—S—CR$^9$R$^{10}$— wherein R$^7$, R$^8$, R$^9$, R$^{10}$, R$^{11}$, R$^{12}$, R$^{13}$ and R$^{14}$ are independently hydrogen or $C_1$–$C_8$ alkyl and p and q are independently zero or 1;

Y is selected from the group consisting of CR$^{15}$R$^{16}$, NR$^{17}$, O and S, wherein R$^{15}$ and R$^{16}$ are independently hydrogen or $C_1$–$C_8$ alkyl, and R$^{17}$ is hydrogen, $C_1$–$C_8$ alkyl, $C_2$–$C_8$ alkenyl or $C_2$–$C_8$ alkynyl;

Z is selected from the group consisting of NH, O and S; and n is 1, 2 or 3, and pharmaceutically acceptable salts thereof, with the proviso that when Z is NH and X is —CH$_2$—CH$_2$—, then Y is other than NH.

2. A compound having the structural formula (III)

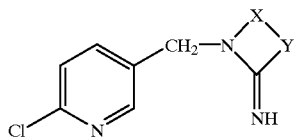

(III)

wherein:
X is selected from the group consisting of —(CH$_2$)$_2$—, —(CH$_2$)$_3$—, —(CH$_2$)$_4$—, —CH=CH—, —CH$_2$—CH(CH$_3$)—, —CH$_2$—CH(C$_2$H$_5$)—, —CH(CH$_3$)—CH$_2$—, —CH(C$_2$H$_5$)—CH$_2$—, —CH$_2$—O—CH$_2$—, —CH$_2$—S—CH$_2$—, —CH$_2$—NH—CH$_2$— and —CH$_2$—N(CH$_3$)—CH$_2$—;
Y is selected from the group consisting of CH$_2$, NH, O and S;
and pharmaceutically acceptable salts thereof, with the proviso that when X is —CH$_2$—CH$_2$—, Y is other than NH.

3. The compound of claim 2, wherein:
X is —(CH$_2$)$_2$—, —(CH$_2$)$_3$— or —CH=CH—.

4. The compound of claim 3, wherein X is —(CH$_2$)$_2$—.

5. The compound of claim 3, wherein X is —(CH$_2$)$_3$—.

6. A pharmiaceutical formulation for treating a mammalian individual suffering from a CNS disorder that is responsive to administration of an m-nAChR modulator, comprising a therapeutically effective amount of the compound of claim 1 and a pharmaceutically acceptable carrier.

7. A pharmaceutical formulation for treating a mammalian individual suffering from a CNS disorder that is responsive to administration of an m-nAChR modulator, comprising a therapeutically effective amount of the compound of claim 2 and a pharmaceutically acceptable carrier.

8. The formulation of claim 6, wherein the CNS disorder is Alzheimer's disease.

9. The formulation of claim 7, wherein the CNS disorder is Alzheimer's disease.

10. A method for treating a mammalian individual suffering from a CNS disorder that is responsive to administration of an m-nAChR modulator, comprising administering to the individual a therapeutically effective amount of the compound of claim 1.

11. A method for treating a mammalian individual suffering from a CNS disorder that is responsive to administration of an m-nAChR modulator, comprising administering to the individual a therapeutically effective amount of the compound of claim 2.

12. The method of claim 10, wherein the CNS disorder is Alzheimer's disease.

13. The method of claim 11, wherein the CNS disorder is Alzheimer's disease.

14. The compound of claim 3, wherein X is —CH=CH—.

* * * * *